United States Patent
Kent

(10) Patent No.: US 10,765,862 B2
(45) Date of Patent: Sep. 8, 2020

(54) SYSTEMS AND METHODS FOR TREATING SLEEP DISORDERED BREATHING

(71) Applicant: Vanderbilt University, Nashville, TN (US)

(72) Inventor: David T. Kent, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 67 days.

(21) Appl. No.: 16/137,865

(22) Filed: Sep. 21, 2018

(65) Prior Publication Data

US 2019/0117966 A1 Apr. 25, 2019

Related U.S. Application Data

(60) Provisional application No. 62/576,377, filed on Oct. 24, 2017.

(51) Int. Cl.
| | |
|---|---|
| *A61N 1/00* | (2006.01) |
| *A61N 1/36* | (2006.01) |
| *A61B 5/00* | (2006.01) |
| *A61B 5/08* | (2006.01) |
| *A61N 1/05* | (2006.01) |
| *A61F 5/56* | (2006.01) |
| *A61B 5/113* | (2006.01) |

(52) U.S. Cl.
CPC .......... *A61N 1/3601* (2013.01); *A61B 5/0826* (2013.01); *A61B 5/4818* (2013.01); *A61N 1/36003* (2013.01); *A61N 1/3611* (2013.01); *A61N 1/36139* (2013.01); *A61B 5/0816* (2013.01); *A61B 5/113* (2013.01); *A61B 5/4815* (2013.01); *A61B 5/4836* (2013.01); *A61F 5/56* (2013.01); *A61N 1/0548* (2013.01)

(58) Field of Classification Search
CPC ................ A61N 1/0548; A61N 1/3601; A61N 1/36139; A61N 1/3611
See application file for complete search history.

(56) References Cited

U.S. PATENT DOCUMENTS

| | | |
|---|---|---|
| 2005/0267547 A1 | 12/2005 | Knudson et al. |
| 2010/0094379 A1* | 4/2010 | Meadows ............ A61N 1/3601 607/48 |
| 2011/0202119 A1* | 8/2011 | Ni ........................ A61N 1/3601 607/116 |
| 2017/0120050 A1 | 5/2017 | Meadows et al. |
| 2017/0128002 A1 | 5/2017 | Christopherson et al. |
| 2017/0151432 A1 | 6/2017 | Christopherson et al. |
| 2017/0224987 A1 | 8/2017 | Kent et al. |

OTHER PUBLICATIONS

Carlson, Dawn M., et al. "Palatal muscle electromyogram activity in obstructive sleep apnea." American journal of respiratory and critical care medicine 152.3 (1995): 1022-1027.

(Continued)

*Primary Examiner* — Mallika D Fairchild
(74) *Attorney, Agent, or Firm* — Tarolli, Sundheim, Covell & Tummino LLP

(57) ABSTRACT

Methods and systems for treating sleep disordered breathing by stimulating nerves that innervate the palatoglossus and/or the palatopharyngeus muscle are provided. Such therapy can be used in conjunction with hypoglossal nerve stimulation.

8 Claims, 2 Drawing Sheets

(56) References Cited

OTHER PUBLICATIONS

Heiser, Clemens, et al. "Palatoglossus coupling in selective upper airway stimulation." The Laryngoscope 127.10 (2017): E378-E383.

Kuehn, D. P., and N. A. Azzam. "Anatomical characteristics of palatoglossus and the anterior faucial pillar." The Cleft palate journal 15.4 (1978): 349-359.

Mathur, Rajat, et al. "Effect of breathing, pressure and posture on palatoglossal and genioglossal tone." Clinical science 89.4 (1995): 441-445.

Mortimore, I. L., R. Mathur, and N. J. Douglas. "Effect of posture, route of respiration, and negative pressure on palatal muscle activity in humans." Journal of Applied Physiology 79.2 (1995): 448-454.

Perry, Jamie L. "Anatomy and physiology of the velopharyngeal mechanism." Seminars in speech and language. vol. 32. No. 02. © Thieme Medical Publishers, 2011.

Sakamoto, Yujiro. "Configuration of the extrinsic muscles of the tongue and their spatial interrelationships." Surgical and Radiologic Anatomy 39.5 (2017): 497-506.

Strollo, Jr, Patrick J., et al. "Upper-airway stimulation for obstructive sleep apnea." New England Journal of Medicine 370.2 (2014): 139-149.

\* cited by examiner

100

Placing an electrode into electrical communication with a target site of a nerve that innervates a palatoglossus muscle, a target site of a nerve that innervates a palatopharyngeus muscle, or both
102

Activating the electrode to deliver an electrical signal to the target site to improve the patient's SBD
104

SYSTEMS AND METHODS FOR TREATING SLEEP DISORDERED BREATHING

RELATED APPLICATION

This application claims priority from U.S. Provisional Application No. 62/576,377, filed 24 Oct. 2017, the subject matter of which is incorporated herein by reference in its entirety.

TECHNICAL FIELD

Methods and systems for treating sleep disordered breathing by stimulating nerves that innervate the palatoglossus and/or the palatopharyngeus muscle are provided.

BACKGROUND

Sleep disordered breathing (SBD) occurs when there is a partial or complete cessation of breathing that occurs many times throughout the night. Obstructive sleep apnea (OSA) is a type of SBD that involves cessation or significant decrease in airflow in the presence of breathing effort. It is the most common type of SBD and is characterized by recurrent episodes of upper airway collapse during sleep inducing repetitive pauses in breathing followed by reductions in blood oxygen saturation. The pathophysiology of OSA can involve factors such as craniofacial anatomy, airway collapsibility, and neuromuscular control of the upper airway dilator musculature. Electromyogram studies have shown that the tonic and phasic activity of the main pharyngeal airway dilatory muscle (such as the genioglossus muscle) is progressively reduced from wakefulness to non-rapid eye movement to rapid eye movement.

Continuous positive airway pressure (CPAP) therapy is the frontline treatment for OSA. CPAP therapy utilizes machines, generally including a flow generator, tubing, and a mask designed to deliver a constant flow of air pressure to keep the airways continuously open in patients with OSA. However, the success of CPAP therapy is limited by compliance with reported rates ranging from 50% to 70%. Hypoglossal nerve stimulation (HNS) has now been established as an effective form of therapy for patients with obstructive sleep apnea (OSA) who are unable to tolerate positive airway pressure. This therapy works by protruding and stiffening the tongue muscle thereby dilating the pharyngeal airway. HNS primarily dilates the hypopharyngeal airway, and has a more modest and variable effect on dilation of the retropalatal airway. Patients with significant retropalatal airway collapse (more specifically, circumferential palatal collapse) are not candidates for the only HNS therapy commercially available in the US because of this issue.

SUMMARY

The present disclosure relates to methods and systems for treating SBD by stimulating nerves that innervate palatal muscles. In an aspect, a method for improving SBD in a patient suffering therefrom comprises placing an electrode into electrical communication with a target site of a nerve that innervates a palatoglossus muscle, a target site of a nerve that innervates a palatopharyngeus muscle, or both. The method further comprises activating the electrode to deliver an electrical signal to the target site to improve the patient's SBD.

In another aspect, a therapy delivery system for improving SBD comprises an electrode configured to deliver an electrical signal to a target site of a nerve that innervates a palatoglossus muscle, a target site of a nerve that innervates a palatopharyngeus muscle, or both. The system further includes a power source in electrical communication with the electrode. The system also includes a controller in electrical communication with the electrode and programmed to direct delivery of an electrical signal by the electrode to the target site to improve the SBD.

In another aspect, a closed-loop therapy delivery system for improving SBD comprises an electrode configured to deliver a therapy signal to a target site of a nerve that innervates a palatoglossus muscle, a target site of a nerve that innervates a palatopharyngeus muscle, or both. The system also includes a power source in electrical communication with the electrode. The system further includes a sensor in electrical communication with the electrode and configured to sense a physiological parameter associated with the SBD and to generate a sensor signal based on the physiological parameter. The system also includes a controller that is in electrical communication with the electrode and the sensor. The controller is programmed to direct delivery of the therapy signal to the target site by the electrode based on the sensor signal to improve the SBD.

DETAILED DESCRIPTION

The present disclosure relates to systems and methods for improving SBD by stimulating a nerve that innervates a palatal muscle. Non-limiting examples of SBDs are increased upper airway resistance including snoring; upper airway resistance syndrome (UARS); and sleep apnea. Sleep apnea can include OSA, central sleep apnea (CSA), and mixed sleep apnea. As used herein with respect to a described element, the terms "a," "an," and "the" include at least one or more of the described element unless otherwise indicated. Further, the terms "or" and "and" refer to "and/or" and combinations thereof unless otherwise indicated. As used herein with respect to a target site, the term "electrical communication" refers to the ability of an electric field generated by an electrode to be transferred to the target site. The electrode can be positioned in direct electrical communication with a target site such that electrode is adjacent to the target site to directly stimulate the target site. Such direct electrical stimulation is in contrast to an electrode being placed adjacent to a site distal or proximal to the target site and thus directly stimulating such distal or proximal sites and indirectly stimulating the target site. Reference to "improving" a patient's SBD includes treating, reducing the symptoms of, mitigating, or preventing the SBD. As used herein, "stimulating" or "stimulate" refers to exciting or inhibiting neural activity.

Aspects of the present disclosure involve electrically stimulating a nerve that innervates the palatoglossus muscle, the palatopharyngeus muscle, or both to improve SBD in a patient suffering therefrom. The palatoglossus muscle and palatopharyngeus muscle are muscles of the soft palate (also referred to as "palatal muscles"). The palatoglossus muscle originates from the palatine aponeurosis at the posterior part of the hard palate. It descends inferolaterally to insert into the posterolateral surface of the tongue. During its course through the posterior part of the oral cavity, it is covered medially by a mucous membrane, so forming the palatoglossus arch. The palatoglossus muscle functions to close off the oral cavity from the oropharynx by elevating the posterior tongue and drawing the soft palate inferiorly. Without wishing to be bound by theory, this muscle is innervated by a branch of the pharyngeal plexus, which functions independently of the hypoglossal nerve and the rest of the intrinsic and extrinsic tongue musculature. The palatopharyngeus muscle forms the palatopharyngeal arch. It attaches superiorly to the hard palate and palatine aponeurosis and inferiorly to the lateral wall of the pharynx. It functions to tense the soft palate and pull the pharyngeal walls superiorly, anteriorly, and medially during swallowing, effectively closing off the nasopharynx from the oropharynx.

Figure 1:
FIG. 1 is a flow chart depicting illustrative steps of a method of improving SBD in a patient suffering therefrom according to an embodiment of the present disclosure.

Referring to FIG. 1, in an embodiment, a method 100 of improving SBD in a patient suffering therefrom comprises placing an electrode into electrical communication with a target site of a nerve that innervates a palatoglossus muscle, a target site of a nerve that innervates a palatopharyngeus muscle, or both (102). Method 100 further includes activating the electrode to deliver an electrical signal to the target site to improve the patient's SBD (104). Such a methodology is different than indirect methods of muscle stimulation such as transcutaneous electrical pacing, which have been found to be inconsistent and poorly tolerated by sleeping patients. Direct intramuscular stimulation via fine wire electrode placement or other techniques would be impractical for daily use as it would require daily uncomfortable piercing of the skin or lining of the mouth to access muscle tissue. Without wishing to be bound by theory, electrical stimulation of a nerve that innervates the palatoglossus muscle and/or palatopharyngeus muscle during sleep can dilate the retropalatal space and therefore open the patient's upper airway without causing arousal from sleep. Such a method can be utilized in patients with isolated palatal collapse or in conjunction with hypoglossal nerve stimulation as part of multi-level airway therapy for SBD, such as OSA. Regarding the latter, methods as disclosed herein can also include stimulating a target site of the hypoglossal nerve in conjunction with stimulating a target site of a nerve that innervates a palatoglossus muscle and/or a target site of a nerve that innervates a palatopharyngeus muscle.

In certain embodiments, the target site of a nerve that innervates the palatoglossus muscle and/or the palatopharyngeus muscle is a branch of the pharyngeal plexus. Preferably, the electrical signal delivered to a target site of a nerve that innervates the palatoglossus muscle and/or the palatopharyngeus muscle stimulates motor fibers of the pharyngeal plexus that innervate the patient's soft palate. In certain embodiments, the target site is not a cranial root of an accessory nerve of the patient as targeting the cranial root of the accessory nerve or the root of the vagus nerve would result in diffuse, non-specific stimulation. For example, activation of the vagal root could simultaneously activate the levator veli palatini muscle, which opposes the action of the palatoglossus and palatopharyngeus muscles. Stimulation of the cranial root of the spinal accessory nerve could similarly cause non-specific activation of the pharyngeal plexus musculature. Moreover, the cranial root of the accessory nerve is not known to join the vagus nerve in all patients. If the cranial root of the accessory nerve did not join the pharyngeal plexus it would instead remain with the spinal root of the accessory nerve. Stimulation of the cranial root of the accessory nerve would therefore cause unintentional stimulation of the spinal root of the accessory nerve, which would cause undesirable activation of the sternocleidomastoid and trapezius muscles.

Methods as disclosed herein can be used as part of a closed-loop system (as described in more detail below). Such a method can include sensing a physiological parameter associated with SBD, generating a sensor signal based on the physiological parameter, and activating the electrode to adjust application of the electrical signal to the target site in response to the sensor signal to improve the patient's SBD.

Figure 2:
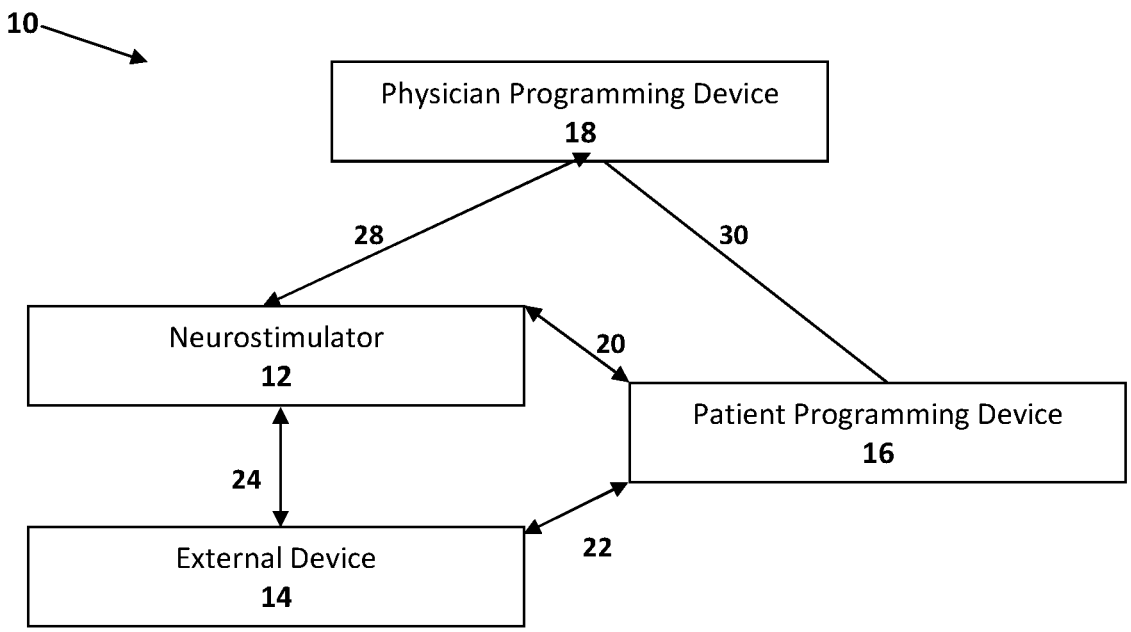
FIG. 2 is block diagram depicting illustrative components of a neurostimulation system according to an embodiment of the present disclosure.
Figure 3:
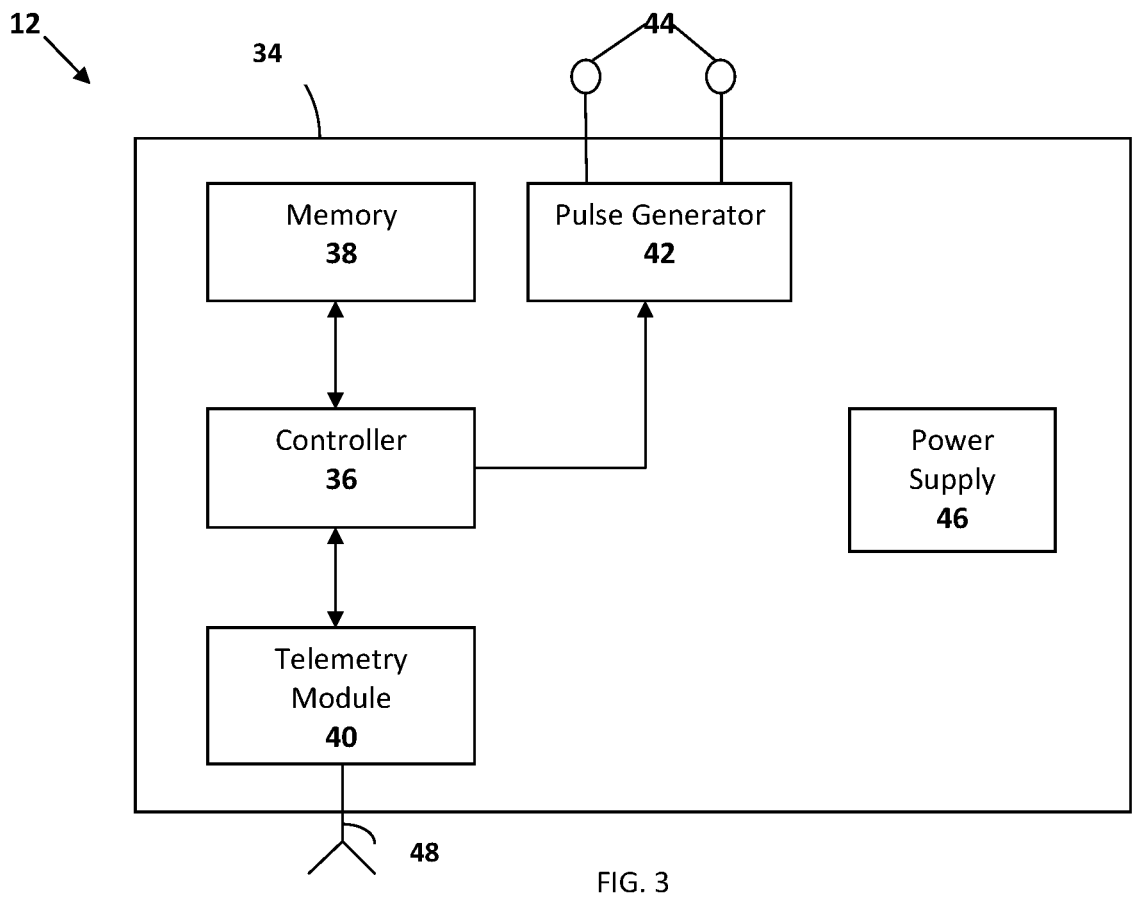
FIG. 3 is a block diagram depicting illustrative components of a neurostimulator according to an embodiment of the present disclosure.

Aspects of the present disclosure also provide systems for improving SBD in a patient suffering therefrom. With reference to FIGS. 2 and 3, in an embodiment, a neurostimulation system 10 includes an implantable neurostimulator 12, an external device 14 that transmits signals to neurostimulator 12, a patient programming device 16 that bidirectionally communicates with neurostimulator 12 and/or an external device 14, and a physician programming device 18. As discussed below, each component of a system can be in communication (e.g., electrical communication) with one another. In some instances, two or more components of a system can be in wireless communication with one another. In other instances, two or more components of a system can be in wired communication with one another. As such, some components of a system can be in wireless communication with one another while other components are in wired communication with one another. Further, in the illustrative embodiments disclosed herein, communication between components included in neurostimulation system 10 is configured to be bidirectional in nature. However, communication between two or more system components can be unidirectional. Further, the functionality of different components of the system can be combined into a single device. For example, the functionality of components of the external device and the patient programming device can be combined into a single device.

In an embodiment, neurostimulator 12 includes electronic circuitry, such as one or more electronic circuits, for delivering neurostimulation pulses enclosed in a sealed housing and coupled to therapy delivery electrodes. In certain embodiments, neurostimulator 12 can include a primary battery cell, a rechargeable battery cell, or an inductively coupled power source for providing power for generating and delivering stimulation pulses and powering other device functions such as communication functions. Neurostimulator 12 or system 10 can include fixation members to secure the neurostimulator to tissue adjacent to the target site.

External device 14 can be a wearable device including a strap, patch or another attachment member(s) for securing external device 14 to the patient in operable proximity to neurostimulator 12. In some instances, external device 14 can be programmed to provide user feedback to assist the patient in optimizing placement of external device 14 about the subject's body. When neurostimulator 12 is provided with a rechargeable battery cell, external device 14 can include a recharging unit for transmitting power, for example inductive power transmission, from external device 14 to neurostimulator 12. In this embodiment, programming device 16 can be a patient handheld device that is used to initiate and terminate therapy delivered by neurostimulator 12 via a bidirectional wireless telemetry link 20. Alternatively, programming device 16 can be operated by a patient for communicating with wearable external device 14 to control therapy on and off times and other therapy control parameters, which are transmitted to neurostimulator 12 via communication link 24. Programming device 16 can communicate with wearable external device 14 via a bidirectional wireless telemetry link 22 that can establish communication over a distance of up to a few feet, enabling distance telemetry such that the patient need not position programming device 16 directly over neurostimulator 12 to control therapy on and off times or perform other interrogation or programming operations (e.g., programming of other therapy control parameters).

When neurostimulator 12 includes primary cell(s), external device 14 can be optional. Programming of neurostimulator 12 can be performed by programming device 16, using near- or distance-telemetry technology for establishing a bidirectional communication link 20 for transmitting data between programming device 16 and neurostimulator 12. Programming device 16 can be used by a patient or clinician to set a therapy protocol that is performed automatically by neurostimulator 12. Programming device 16 can be used to manually start and stop therapy, adjust therapy delivery parameters, and collect data from neurostimulator 12, e.g. data relating to total accumulated therapy delivery time or other data relating to device operation or measurements taken by neurostimulator 12. For example, programming device 16 can include software programmed to control one or more stimulation and/or control parameters associated with neurostimulator 12. Additionally, or optionally, the software comprising programming device 16 can be programmed to store patient therapy data, such as diary questions or physiologic measurements. Programming device 16 can also include software programmed to access remote data sources, query certain data, and then provide stimulation instructions to system 10 based on the queried data. For example, programming device 16 can include software programmed to provide neurostimulator 12 with customizable or patient-triggered alerts, e.g., indicating stimulation periods and the duration of each period, after a desired period of time (e.g., 30 minutes) after sleep onset. Programming device 16 can be embodied as a smart phone or tablet, although personal computers (PCs) may also be included.

When neurostimulator 12 is configured as an externally powered device, external device 14 can be a power transmission device that is worn by the patient during sleep to provide power needed to generate stimulation pulses. For example, external device 14 can be a battery-powered device including a primary coil used to inductively transmit power to a secondary coil included in neurostimulator 12. External device 14 can include one or more primary and/or rechargeable cells and therefore can include a power adaptor and plug for re-charging in a standard 110V or 220V wall outlet, for example.

In some embodiments, the functionality required for transmitting power to neurostimulator 12 when neurostimulator 12 is embodied as a rechargeable or externally powered device and for programming the neurostimulator 12 for controlling therapy delivery can be implemented in a single external device. For example, power transmission capability of external device 14 and programming capabilities of patient programmer 16 can be combined in a single external device, which can be a wearable or handheld device (such as, for example, a smart phone or tablet).

Physician programming device 18 can include increased programming and diagnostic functionality compared to patient programming device 16. For example, physician programming device 18 can be configured for programming all neurostimulation therapy control parameters, such as, but not limited to, pulse amplitude, pulse width, pulse shape, pulse frequency, duty cycle, therapy on and off times, electrode selection, and electrode polarity assignments. Patient programming device 16 can be limited to turning therapy on and/or off, adjusting a start time of therapy, and/or adjusting a pulse amplitude without giving the patient full access to full programming functions such that some programming functions and programmable therapy control parameters cannot be accessed or altered by a patient.

Physician programming device 18 can be configured to communicate directly with neurostimulator 12 via wireless, bidirectional telemetry link 28 for example during an office visit. Additionally or alternatively, physician programming device 18 can be operable as a remote programming instrument used to transmit programming commands to patient programming device 16 via a wired or wireless communication network link 30, after which patient programming device 16 automatically transmits programming data to neurostimulator 12 via bidirectional telemetry link 20 (or via wearable external device 14 and link 24). Physician programming device can be embodied as a smart phone, tablet or PC, for example.

In some embodiments, the patient can be provided with a magnet for adjusting operation of neurostimulator 12. For example, application of the magnet can turn therapy on or off or cause other binary or stepwise adjustments to neurostimulator 12 operations.

FIG. 3 is a functional block diagram of neurostimulator 12 of FIG. 2 according to an embodiment of a neurostimulation system. Neurostimulator 12 can include a housing 34 enclosing a controller 36 and associated memory 38, a telemetry module 40, and a pulse generator 42 coupled to electrode(s) 44. Neurostimulator 12 includes a power supply 46, which as described above can include any of a primary battery cell, a rechargeable battery cell, and/or a secondary coil of an externally powered system.

Controller 36 can include any one or more of a microprocessor, a digital signal processor (DSP), an application specific integrated circuit (ASIC), a field-programmable gate array (FPGA), or equivalent discrete or integrated logic circuitry. In some examples, controller 36 can include multiple components, such as any combination of one or more microprocessors, one or more controllers, one or more DSPs, one or more ASICs, or one or more FPGAs, as well as other discrete or integrated logic circuitry. The functions attributed to controller 36 herein can be embodied as software, firmware, hardware or any combination thereof. In one example, a neurostimulation therapy protocol to improve an SBD in a patient can be stored or encoded as instructions in memory 38 that are executed by controller 36 to cause pulse generator 42 to deliver the therapy via electrodes 44 according to the programmed protocol.

Memory 38 can include computer-readable instructions that, when executed by controller 36, cause neurostimulator 12 to perform various functions attributed throughout this disclosure to the neurostimulator. The computer-readable instructions can be encoded within memory 38. Memory 38 can comprise non-transitory computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory, propagating signal.

Telemetry module 40 and associated antenna 48 can be provided for establishing bidirectional communication with external device 14, patient programmer 16 and/or physician programmer 18. Examples of communication techniques used by neurostimulator 12 and programming device 16 or 18 include low frequency or radiofrequency (RF) telemetry, which can be an RF link established via Bluetooth, WiFi, or MICS, for example. Antenna 48 can be located within, along or extend externally from housing 34.

Electrodes 44 can be located along an exterior surface of housing 44 and can be coupled to pulse generator 42 via insulated feedthroughs or other connections as will be further described below. In other embodiments, electrodes 44 can be carried by a lead or insulated tether electrically coupled to pulse generator 42 via appropriate insulated feedthroughs or other electrical connections crossing sealed housing 34. In still other embodiments, electrodes 44 can be incorporated in housing 34 with externally exposed surfaces adapted to be operably positioned in proximity to a target site of a nerve innervating a palatoglossus muscle and/or a palatopharyngeus muscle and electrically coupled to pulse generator 42. In certain embodiments, electrodes configured to stimulate a target site of a nerve innervating the palatoglossus muscle and/or the palatopharyngeus muscle can be located on the same neurostimulator, such as the same lead or nerve cuffs for example. Alternatively, electrodes configured to stimulate a target site of a nerve innervating the palatoglossus muscle and/or the palatopharyngeus muscle can be located on different neurostimulator, such as different leads or nerve cuffs, for example. In certain embodiments, electrodes configured to stimulating a nerve innervating the palatoglossus and/or the palatopharyngeus muscle are combined with a neurostimulator configured to stimulate the hypoglossal nerve. Still alternatively, electrodes configured to stimulate a nerve innervating the palatoglossus and/or the palatopharyngeus muscle can be part of a device separate from a device configured to stimulate the hypoglossal nerve.

In another aspect, system 10 can include one or more sensors (not shown) to permit open- or closed-loop control. In an open-loop system, for example, system 10 can include one or more sensors such that a patient can manage (e.g., prophylactically) improvement of the SBD based on feedback (e.g., detected signals) from the sensor(s). Such detected signals can be indicative of the onset of the SBD, such as changes in muscle or nerve electrical activity, tongue position, oropharyngeal airflow, etc. Upon noticing the signal(s), the patient can then trigger or activate the neurostimulator 12 to prevent or mitigate the SBD.

In another aspect, system 10 can include one or more sensors to permit closed-loop control by, for example, automatically responding (e.g., by activation of the neurostimulator 12) in response to a sensed physiological parameter, or a related symptom or sign, indicative of the extent and/or presence of the SBD. Physiological parameters include changes in muscle or nerve electrical activity, tongue position, oropharyngeal airflow, etc. Sensors used as part of a closed- or open-loop system can be placed at any appropriate anatomical location on a patient, including a skin surface, an oral cavity, a nasal cavity, a mucosal surface, or at a subcutaneous location.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

What is claimed is:

1. A method for improving obstructive sleep apnea (OSA) in a patient suffering therefrom comprising:
   placing an electrode into electrical communication with a target site of a nerve that is a branch of a pharyngeal nerve plexus that innervates a palatoglossus muscle, a palatopharyngeus muscle, or both of the patient, the target site of the nerve not being a cranial root of an accessory nerve of the patient; and
   activating the electrode to deliver an electrical signal to the target site of the nerve to improve the patient's OSA.

2. The method of claim 1, wherein placing an electrode comprises placing an electrode into electrical communication with the target site of the nerve that innervates the palatoglossus muscle.

3. The method of claim 1, wherein placing an electrode comprises placing an electrode into electrical communication with the target site of the nerve that innervates the palatopharyngeus muscle.

4. The method of claim 1, wherein placing an electrode comprises placing an electrode into electrical communication with the target site of the nerve that innervates the palatoglossus muscle and the target site of the nerve that innervates the palatopharyngeus muscle.

5. The method of claim 4, further comprising delivering an electrical signal to a target site of a hypoglossal nerve of the patient.

6. The method of claim 1, further comprising delivering an electrical signal to a target site of a hypoglossal nerve of the patient.

7. The method of claim 1, wherein activating the electrode to deliver an electrical signal to the target site of the nerve that is a branch of the pharyngeal nerve plexus that innervates the palatoglossus muscle and/or palatopharyngeus muscle comprises stimulating motor fibers of the pharyngeal nerve plexus that innervate the patient's soft palate.

8. The method of claim 1, further comprising the steps of:
   sensing a physiological parameter associated with the sleep disordered breathing;
   generating a sensor signal based on the physiological parameter; and
   activating the electrode to adjust application of the electrical signal to the target site in response to the sensor signal to improve the patient's sleep OSA.

* * * * *